(12) United States Patent
Minidis et al.

(10) Patent No.: US 7,476,684 B2
(45) Date of Patent: *Jan. 13, 2009

(54) COMPOUNDS FOR THE TREATMENT OF NEUROLOGICAL, PSYCHIATRIC OR PAIN DISORDERS

(75) Inventors: Alexander Minidis, Södertälje (SE); David Wensbo, Södertälje (SE); Methvin Isaac, Toronto (CA); Abdelmalik Slassi, Toronto (CA); Jalaj Arora, Toronto (CA); Tao Xin, Toronto (CA); Louise Edwards, Toronto (CA); Caroline Eriksson, Eslöv (SE); Veronica Profir, Södertälje (SE); Per-Olov Bergstrom, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/523,717

(22) Filed: Sep. 20, 2006

(65) Prior Publication Data

US 2007/0129408 A1     Jun. 7, 2007

Related U.S. Application Data

(60) Provisional application No. 60/721,527, filed on Sep. 29, 2005.

(51) Int. Cl.
*A61K 31/4439* (2006.01)
*C07D 413/14* (2006.01)

(52) U.S. Cl. .................... 514/340; 546/272.1

(58) Field of Classification Search ............ 546/272.1; 514/340
See application file for complete search history.

(56) References Cited

U.S. PATENT DOCUMENTS

2005/0272779 A1   12/2005   Edwards et al.

FOREIGN PATENT DOCUMENTS

| WO | WO-01/12627 A1 | 2/2001 |
|---|---|---|
| WO | WO-02/068417 A | 9/2002 |
| WO | WO-2005/068417 A2 | 9/2002 |
| WO | WO-2004/014370 A2 | 2/2004 |
| WO | WO-2004/014881 A2 | 2/2004 |
| WO | WO-2004/014902 A2 | 2/2004 |
| WO | WO-2005-060971 A | 7/2005 |
| WO | WO-2005/066155 A1 | 7/2005 |
| WO | WO-2005/077345 A | 8/2005 |
| WO | WO-2005/077368 A2 | 8/2005 |
| WO | WO-2005/080356 A1 | 9/2005 |
| WO | WO-2005/080363 A1 | 9/2005 |
| WO | WO-2005/080379 A1 | 9/2005 |
| WO | WO-2005/080386 A1 | 9/2005 |
| WO | WO-2005/080397 A2 | 9/2005 |
| WO | WO-2006/014185 A1 | 2/2006 |

OTHER PUBLICATIONS

Vippagunta et al., "Crystalline Solids", Advanced Drug Delivery Reviews 48 (2001) 3-26.*
Guillory in Brittain ed, "Polymorphism in Pharmaceutical Solids" NY: Marcel Dekker, Inc., 1999, pp. 183-226.*
Schoepp et al., Trends Pharmacol. Sci. 14:13 (1993).
Schoepp, Neurochem. Int. 24:439 (1994).
Pin et al., Neuropharmacology 34:1 (1995).
Bordi and Ugolini, Prog. Neurobiol. 59:55 (1999).
Nakanishi, Neuron 13:1031 (1994).
Knopfel et al., J. Med. Chem. 38:1417 (1995).
Pin et al., PNAS 89:10331 (1992).
Minakami et al., BBRC 199:1136 (1994).
Joly et al., J. Neurosci. 15:3970 (1995).
Baskys, Trends Pharmacol. Sci. 15:92 (1992).
Watkins et al., Trends Pharmacol. Sci. 15:33 (1994).
Bashir et al., Nature 363:347 (1993).
Bortolotto et al., Nature 368:740 (1994).
Aiba et al., Cell 79:365 (1994).
Aiba et al., Cell 79:377 (1994).
Meller et al., Neuroreport 4:879 (1993).
Bordi and Ugolini, Brain Res. 871:223 (2000).
Cunningham et al., Life Sci. 54:135 (1994).
Hollman et al., Ann. Rev. Neurosci. 17:31 (1994).
Spooren et al., Trends Pharmacol. Sci. 22:331 (2001).
Gasparini et al. Curr. Opin. Pharmacol. 2:43 (2002).
Neugebauer Pain 98:1 (2002).
Holloway & Dent (1990) Gastroenterol. Clin. N. Amer. 19, pp. 517-535.

* cited by examiner

*Primary Examiner*—Patricia L Morris
(74) *Attorney, Agent, or Firm*—Birch, Stewart, Kolasch & Birch LLP

(57) ABSTRACT

The present invention is directed to novel compounds, their use in therapy and pharmaceutical compositions comprising said novel compounds.

5 Claims, No Drawings

COMPOUNDS FOR THE TREATMENT OF NEUROLOGICAL, PSYCHIATRIC OR PAIN DISORDERS

This Non-provisional application claims priority under 35 U.S.C. § 119(e) on U.S. Provisional Application No. 60/721,527 filed on Sep. 29, 2005, the entire contents of which are hereby incorporated by reference.

FIELD OF THE INVENTION

The present invention is directed to novel compounds, their use in therapy and pharmaceutical compositions comprising said novel compounds.

BACKGROUND OF THE INVENTION

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., *Trends Pharmacol. Sci.* 14:13 (1993), Schoepp, *Neurochem. Int.* 24:439 (1994), Pin et al., *Neuropharmacology* 34:1 (1995), Bordi and Ugolini, *Prog. Neurobiol.* 59:55 (1999).

Molecular cloning has identified eight distinct mGluR subtypes, termed mGluR1 through mGluR8. Nakanishi, *Neuron* 13:1031 (1994), Pin et al., *Neuropharmacology* 34:1 (1995), Knopfel et al., *J. Med. Chem.* 38:1417 (1995). Further receptor diversity occurs via expression of alternatively spliced forms of certain mGluR subtypes. Pin et al., *PNAS* 89:10331 (1992), Minakami et al., *BBRC* 199:1136 (1994), Joly et al., *J. Neurosci.* 15:3970 (1995).

Metabotropic glutamate receptor subtypes may be subdivided into three groups, Group I, Group II, and Group III mGluRs, based on amino acid sequence homology, the second messenger systems utilized by the receptors, and by their pharmacological characteristics. Group I mGluR comprises mGluR1, mGluR5 and their alternatively spliced variants. The binding of agonists to these receptors results in the activation of phospholipase C and the subsequent mobilization of intracellular calcium.

Neurological, Psychiatric and Pain Disorders

Attempts at elucidating the physiological roles of Group I mGluRs suggest that activation of these receptors elicits neuronal excitation. Various studies have demonstrated that Group I mGluRs agonists can produce postsynaptic excitation upon application to neurons in the hippocampus, cerebral cortex, cerebellum, and thalamus, as well as other CNS regions. Evidence indicates that this excitation is due to direct activation of postsynaptic mGluRs, but it also has been suggested that activation of presynaptic mGluRs occurs, resulting in increased neurotransmitter release. Baskys, *Trends Pharmacol. Sci.* 15:92 (1992), Schoepp, *Neurochem. Int.* 24:439 (1994), Pin et al., *Neuropharmacology* 34:1(1995), Watkins et al., *Trends Pharmacol. Sci.* 15:33 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993), Bortolotto et al., *Nature* 368:740 (1994), Aiba et al., *Cell* 79:365 (1994), Aiba et al., *Cell* 79:377 (1994). A role for mGluR activation in nociception and analgesia also has been demonstrated, Meller et al., *Neuroreport* 4: 879 (1993), Bordi and Ugolini, *Brain Res.* 871:223 (1999). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex. Nakanishi, *Neuron* 13: 1031 (1994), Pin et al., *Neuropharmacology* 34:1, Knopfel et al., *J. Med. Chem.* 38:1417 (1995).

Further, Group I metabotropic glutamate receptors and mGluR5 in particular, have been suggested to play roles in a variety of pathophysiological processes and disorders affecting the CNS. These include stroke, head trauma, anoxic and ischemic injuries, hypoglycemia, epilepsy, neurodegenerative disorders such as Alzheimer's disease and pain. Schoepp et al., *Trends Pharmacol. Sci.* 14:13 (1993), Cunningham et al., *Life Sci.* 54:135 (1994), Hollman et al., *Ann. Rev. Neurosci.* 17:31 (1994), Pin et al., *Neuropharmacology* 34:1 (1995), Knopfel et al., *J. Med. Chem.* 38:1417 (1995), Spooren et al., *Trends Pharmacol. Sci.* 22:331 (2001), Gasparini et al. *Curr. Opin. Pharmacol.* 2:43 (2002), Neugebauer *Pain* 98:1 (2002). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial, specifically as neuroprotective agents, analgesics or anticonvulsants.

Recent advances in the elucidation of the neurophysiological roles of metabotropic glutamate receptors generally and Group I in particular, have established these receptors as promising drug targets in the therapy of acute and chronic neurological and psychiatric disorders and chronic and acute pain disorders.

Gastrointestinal Disorders

The lower esophageal sphincter (LES) is prone to relaxing intermittently. As a consequence, fluid from the stomach can pass into the esophagus since the mechanical barrier is temporarily lost at such times, an event hereinafter referred to as "reflux".

Gastro-esophageal reflux disease (GERD) is the most prevalent upper gastrointestinal tract disease. Current pharmacotherapy aims at reducing gastric acid secretion, or at neutralizing acid in the esophagus. The major mechanism behind reflux has been considered to depend on a hypotonic lower esophageal sphincter. However, e.g. Holloway & Dent (1990) *Gastroenterol. Clin. N. Amer.* 19, pp. 517-535, has shown that most reflux episodes occur during transient lower esophageal sphincter relaxations (TLESRs), i.e. relaxations not triggered by swallows. It has also been shown that gastric acid secretion usually is normal in patients with GERD.

The novel compounds according to the present invention are assumed to be useful for the inhibition of transient lower esophageal sphincter relaxations (TLESRs) and thus for treatment of gastro-esophageal reflux disorder (GERD).

Because of their physiological and pathophysiological significance, there is a need for new potent mGluR agonists and antagonists that display a high selectivity for mGluR subtypes, particularly the Group I receptor subtype, most particularly the mGluR5

The object of the present invention is to provide compounds exhibiting an activity at metabotropic glutamate receptors (mGluRs), especially at the mGluR5 receptor.

DESCRIPTION OF THE INVENTION

One embodiment of the present invention relates to a compound of formula I:

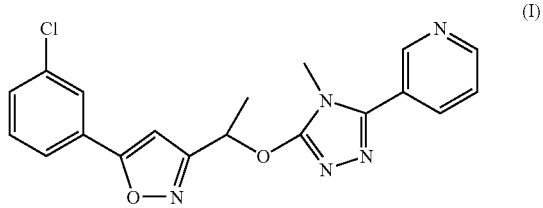

(I)

as well as pharmaceutically acceptable salts, hydrates, isoforms and/or enantiomers thereof. In one embodiment, the compound of formula I is the R-enantiomer. In another embodiment, the compound of formula I is the S-enantiomer.

A further embodiment of the present invention relates to a compound of formula II:

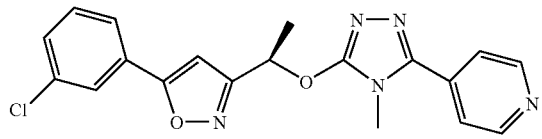

(II)

as well as pharmaceutically acceptable salts, hydrates and/or isoforms thereof.

Yet another embodiment of the present invention relates to a compound of formula III:

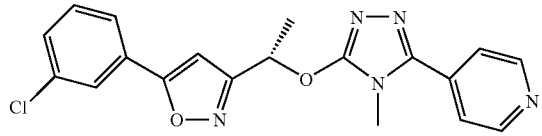

(III)

as well as pharmaceutically acceptable salts, hydrates and/or isoforms thereof.

Another embodiment is a pharmaceutical composition comprising as active ingredient a therapeutically effective amount of the compound according to formula I-III, in association with one or more pharmaceutically acceptable diluents, excipients and/or inert carriers.

Other embodiments, as described in more detail below, relate to a compound according to formula I-III for use in therapy, in treatment of mGluR5 mediated disorders, in the manufacture of a medicament for the treatment of mGluR5 mediated disorders.

Still other embodiments relate to a method of treatment of mGluR5 mediated disorders, comprising administering to a mammal a therapeutically effective amount of the compound according according to formula I-III.

In another embodiment, there is provided a method for inhibiting activation of mGlurR5 receptors, comprising treating a cell containing said receptor with an effective amount of the compound according to formula I-III.

The compounds of the present invention are useful in therapy, in particular for the treatment of neurological, psychiatric, pain, and gastrointestinal disorders.

It will also be understood by those of skill in the art that certain compounds of the present invention may exist in solvated, for example hydrated, as well as unsolvated forms. It will further be understood that the present invention encompasses all such solvated forms of the compounds of formula I-III.

Within the scope of the invention are also salts of the compounds of formula I-III. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a salt with a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol, with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques. Additionally, quaternary ammonium salts can be prepared by the addition of alkylating agents, for example, to neutral amines.

In one embodiment of the present invention, the compound of formula I-III may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

In further embodiments of the present invention, the compound of formula I-III may be converted to a pharmaceutically acceptable salt or solvate thereof with sulfonic acid, 1,2-ethanedisulfonic acid (both as 1:1 and 2:1), ethanesulfonic acid, nitric acid, 2-mesitylenesulfonic acid, 1,5-naphthalenedisulfonic acid (both as 1:1 and 2:1) or p-xylenesulfonic acid.

Pharmaceutical Composition

The compounds of the present invention may be formulated into conventional pharmaceutical compositions comprising a compound of formula I-III, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or tablet disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, or from about 0.10% w to 50% w, of a compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

The compounds according to the present invention are useful in the treatment of conditions associated with excitatory activation of mGluR5 and for inhibiting neuronal damage caused by excitatory activation of mGluR5. The compounds may be used to produce an inhibitory effect of mGluR5 in mammals, including man.

The Group I mGluR receptors including mGluR5 are highly expressed in the central and peripheral nervous system and in other tissues. Thus, it is expected that the compounds of the invention are well suited for the treatment of mGluR5-mediated disorders such as acute and chronic neurological and psychiatric disorders, gastrointestinal disorders, and chronic and acute pain disorders.

The invention relates to compounds of Formula I-III, as defined hereinbefore, for use in therapy.

The invention relates to compounds of Formula I-III, as defined hereinbefore, for use in treatment of mGluR5-mediated disorders.

The invention relates to compounds of Formula I-III, as defined hereinbefore, for use in treatment of Alzheimer's disease senile dementia, AIDS-induced dementia, Parkinson's disease, amylotropic lateral sclerosis, Huntington's Chorea, migraine, epilepsy, schizophrenia, depression, anxiety, acute anxiety, ophthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, Fragile X, autism, mental retardation, schizophrenia and Down's Syndrome.

The invention relates to compounds of Formula I-III, as defined above, for use in treatment of pain related to migraine, inflammatory pain, neuropathic pain disorders such as diabetic neuropathies, arthritis and rheumatoid diseases, low back pain, post-operative pain and pain associated with various conditions including cancer, angina, renal or billiary colic, menstruation, migraine and gout.

The invention relates to compounds of Formula I-III as defined hereinbefore, for use in treatment of stroke, head trauma, anoxic and ischemic injuries, hypoglycemia, cardiovascular diseases and epilepsy.

The present invention relates also to the use of a compound of Formula I-III as defined hereinbefore, in the manufacture of a medicament for the treatment of mGluR Group I receptor-mediated disorders and any disorder listed above.

One embodiment of the invention relates to the use of a compound according to Formula I-III in the treatment of gastrointestinal disorders.

Another embodiment of the invention relates to the use of a Formula I-III compound for the manufacture of a medicament for inhibition of transient lower esophageal sphincter relaxations, for the treatment of GERD, for the prevention of gastroesophageal reflux, for the treatment regurgitation, for treatment of asthma, for treatment of laryngitis, for treatment of lung disease, for the management of failure to thrive, for the treatment of irritable bowel disease (IBS) and for the treatment of functional dyspepsia (FD).

The wording "TLESR", transient lower esophageal sphincter relaxations, is herein defined in accordance with Mittal, R. K., Holloway, R. H., Penagini, R., Blackshaw, L. A., Dent, J., 1995; *Transient lower esophageal sphincter relaxation. Gastroenterology* 109, pp. 601-610.

The wording "reflux" is herein defined as fluid from the stomach being able to pass into the esophagus, since the mechanical barrier is temporarily lost at such times.

The wording "GERD", gastro-esophageal reflux disease, is herein defined in accordance with van Heerwarden, M. A., Smout A. J. P. M., 2000; *Diagnosis of reflux disease. Baillière's Clin. Gastroenterol.* 14, pp. 759-774.

A further embodiment of the invention relates to the use of a compound according to Formula I-III for the manufacture of a medicament for the treatment of cough. In one embodiment, the cough to be treated is chronic cough. In a further embodiment, the cough to be treated is acute cough. The term chronic cough is defined in accordance with Kardos P et al (The German Respiratory Society's Guideline for the Diagnosis and Treatment of Patients with Acute and Chronic Cough Medizinische Klinik 2004; 99(8):468-75) as a cough that lasts longer than 8 weeks. However, chronic cough can also be defined as a cough lasting longer than 3 weeks or as a cough lasting longer than 2 months. The term "acute cough" is also defined in accordance with the reference above as a cough lasting less than 8 weeks.

The compounds of formula I-III above are useful for the treatment or prevention of obesity or overweight, (e.g., promotion of weight loss and maintenance of weight loss), prevention or reversal of weight gain (e.g., rebound, medication-induced or subsequent to cessation of smoking), for modulation of appetite and/or satiety, eating disorders (e.g. binge eating, anorexia, bulimia and compulsive) and cravings (for drugs, tobacco, alcohol, any appetizing macronutrients or non-essential food items).

The invention also provides a method of treatment of mGluR5-mediated disorders and any disorder listed above, in a patient suffering from, or at risk of, said condition, which comprises administering to the patient an effective amount of a compound of Formula I-III, as hereinbefore defined.

The dose required for the therapeutic or preventive treatment of a particular disorder will necessarily be varied depending on the host treated, the route of administration and the severity of the illness being treated.

In the context of the present specification, the term "therapy" and "treatment" includes prevention or prophylaxis, unless there are specific indications to the contrary. The terms "therapeutic" and "therapeutically" should be construed accordingly.

In this specification, unless stated otherwise, the term "antagonist" and "inhibitor" shall mean a compound that by any means, partly or completely, blocks the transduction pathway leading to the production of a response by the ligand.

The term "disorder", unless stated otherwise, means any condition and disease associated with metabotropic glutamate receptor activity.

Non-Medical Use

In addition to their use in therapeutic medicine, the compounds of Formula I-III, as well as salts and hydrates of such compounds, are useful as pharmacological tools in the development and standardization of in vitro and in vivo test systems for the evaluation of the effects of inhibitors of mGluR related activity in laboratory animals such as cats, dogs, rabbits, monkeys, rats and mice, as part of the search for new therapeutic agents.

Methods of Preparation

Synthesis of Intermediates

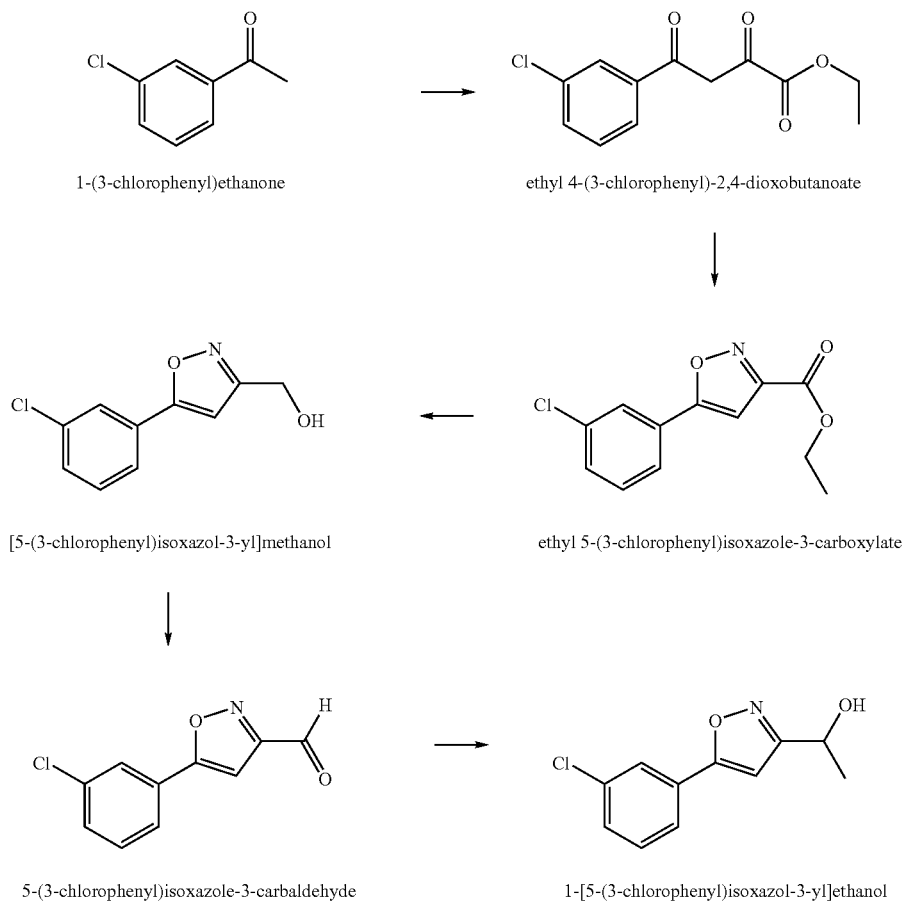

-continued

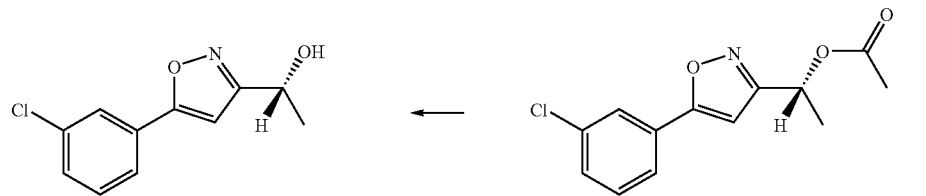

(1R)-1-[5-(3-chlorophenyl)isoxazol-3-yl]ethanol      (1R)-1-[5-(3-chlorophenyl)isoxazol-3-yl]ethyl acetate

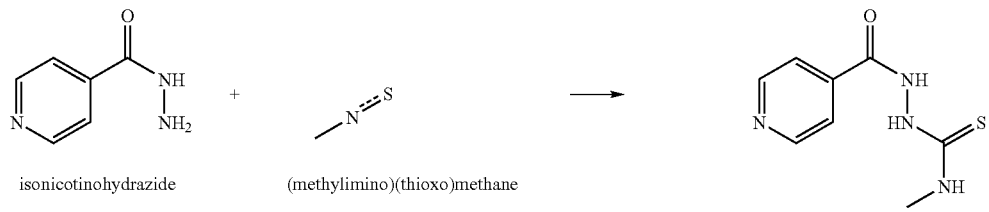

isonicotinohydrazide    (methylimino)(thioxo)methane      2-isonicotinoyl-N-methylhydrazinecarbothioamide

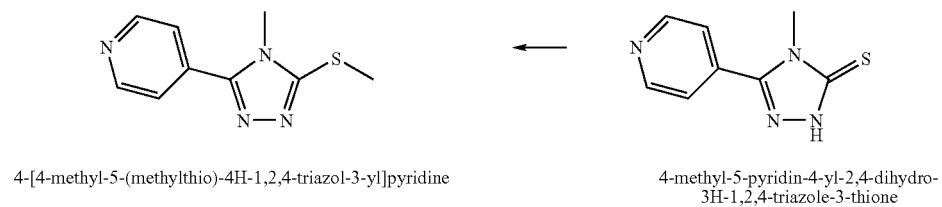

4-[4-methyl-5-(methylthio)-4H-1,2,4-triazol-3-yl]pyridine      4-methyl-5-pyridin-4-yl-2,4-dihydro-3H-1,2,4-triazole-3-thione

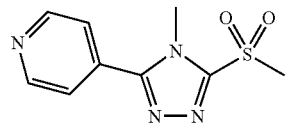

4-[4-methyl-5-(methylsulfonyl)-4H-1,2,4-triazol-3-yl]pyridine

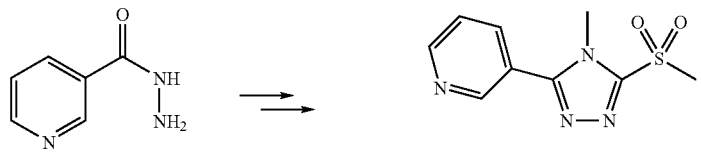

nicotinohydrazide      3-[4-methyl-5-(methylsulfonyl)-4H-1,2,4-triazol-3-yl]pyridine

Synthesis of Final Compounds

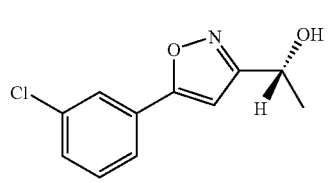
(1R)-1-[5-(3-chlorophenyl)isoxazol-3-yl]ethanol

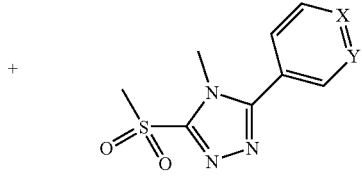
X = N, Y = C: 4-[4-methyl-5-(methylsulfonyl)-4H-1,2,4-triazol-3-yl]pyridine X = C, Y = N: 3-[4-methyl-5-(methylsulfonyl)-4H-1,2,4-triazol-3-yl]pyridine

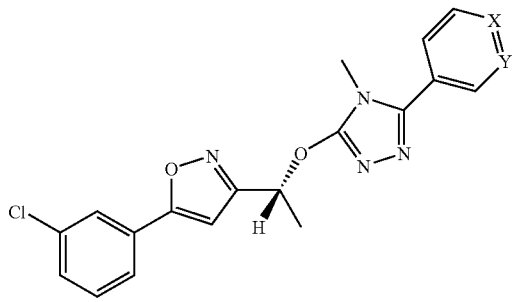

X = N, Y = C: 4-(5-{(1R)-1-[5-(3-chlorophenyl)isoxazol-3-yl]ethoxy}-4-methyl-4H-1,2,4-triazol-3-yl)pyridine
X = C, Y = N: 3-(5-{(1R)-1-[5-(3-chlorophenyl)isoxazol-3-yl]ethoxy}-4-methyl-4H-1,2,4-triazol-3-yl)pyridine

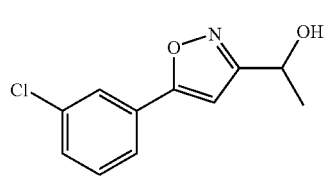
1-[5-(3-chlorophenyl)isoxazol-3-yl]ethanol

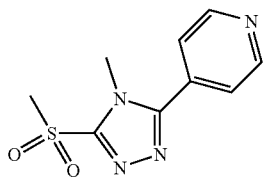
4-[4-methyl-5-(methylsulfonyl)-4H-1,2,4-triazol-3-yl]pyridine

-continued

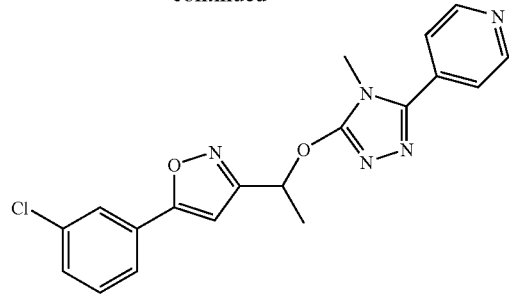

4-(5-{(rac)-1-[5-(3-chlorophenyl)isoxazol-3-yl]ethoxy}-4-methyl-4H-1,2,4-triazol-3-yl)pyridine

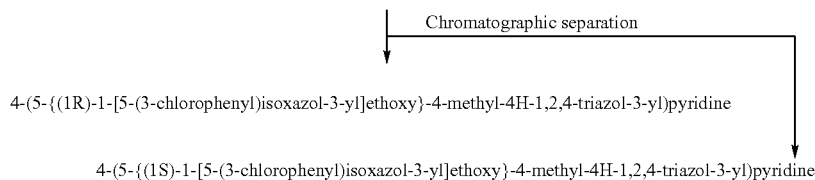

4-(5-{(1R)-1-[5-(3-chlorophenyl)isoxazol-3-yl]ethoxy}-4-methyl-4H-1,2,4-triazol-3-yl)pyridine 4-(5-{(1S)-1-[5-(3-chlorophenyl)isoxazol-3-yl]ethoxy}-4-methyl-4H-1,2,4-triazol-3-yl)pyridine General Methods All starting materials are commercially available or earlier described in the literature. The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet).

Analytical in line liquid chromatography separations followed by mass spectra detections, were recorded on a Waters LC-MS consisting of an Alliance 2795 (LC) and a ZQ single quadropole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 µm, was applied a linear gradient from 5% to 100% acetonitrile in 10 mM ammonium acetate (aq.), or in 0.1% TFA (aq.). Optical rotation was measured with a Perkin Elmer 241 polarimeter, using a 10 cm cell at 23° C. at 589 nm.

LIST OF ABBREVIATIONS aq. Aqueous
DMF dimethyl formamide
EtOAc ethyl acetate
NH$_4$Cl ammonium chloride
Novozyme 435® Registered trademark name for polymer bound candida antarctica lipase
r.t. or RT room temperature (unless otherwise stated, a temperature between 16 to 26° C.)

EXAMPLES

Synthesis of Intermediates

Example 1

Ethyl 4-(3-chlorophenyl)-2,4-dioxobutanoate

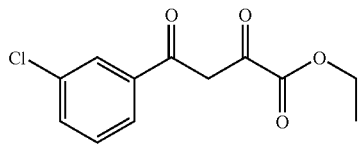

Sodium ethoxide (117.8 g, 1.73 mol) was added in portions to a solution of 3-chloroacetophenone (178.5 g, 1.15 mol) and diethyl oxalate (188 mL, 1.39 mol) in ethanol (3 L) at 0° C. The mixture was stirred at room temperature for 1 h and was then heated at 70° C. for 2 h. After cooling, the mixture was acidified with 3M hydrochloric acid (pH~3). The solvent was distilled off and to the mixture was added EtOAc. The organic layer was washed with water and saturated brine. The solvent was distilled off to give crude title product, which was used directly in the next step. MS (M$^+$−1)=253.

Example 2

Ethyl 5-(3-chlorophenyl)isoxazole-3-carboxylate

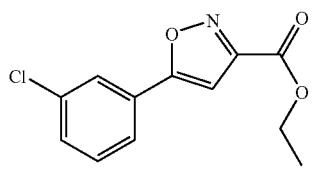

A solution of crude ethyl 4-(3-chlorophenyl)-2,4-dioxobutanoate (max 294 g, 1.16 mol) and hydroxylamine hydrochloride (120.4 g, 1.73 mol) in ethanol (4 L) was heated at 80° C. for 4 h. After cooling (over night) to ca 5-10° C., the mixture was filtered, washed with cold ethanol and dried in vacuo to afford the title compound (214.5 g, 74%). $^1$H NMR: 7.82 (s, 1H), 7.72 (m, 1H), 7.47 (m, 2H), 4.03 (s, 3H). MS ($M^+$+1)=252.

Example 3

[5-(3-chlorophenyl)isoxazol-3-yl]methanol

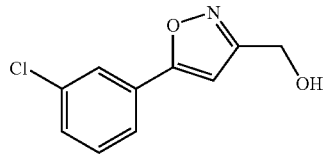

Sodium borohydride (96.7 g, 2.6 mol) was slowly added to a solution of ethyl 5-(3-chlorophenyl)isoxazole-3-carboxylate (214.5 g, 0.85 mol) in methanol (2.5 L) at 0° C. The reaction mixture was heated at 50° C. for 2 h and was quenched with EtOAc at r.t. Most of the solvent was distilled off and to the remaining crude was added EtOAc. The organic layer was washed with water, saturated brine and concentrated to give the title compound, which was used directly in the next step. MS ($M^+$+1)=210.

Example 4

5-(3-chlorophenyl)isoxazole-3-carbaldehyde

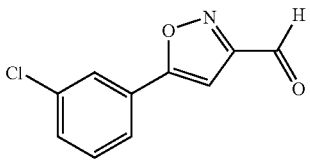

[5-(3-chlorophenyl)isoxazol-3-yl]methanol (178.6 g, 852 mmol) in dichloromethane (2 L) was dropwise added to pyridinium chlorochromate (400 g, 1.86 mol) in dichloromethane (2 L). The resulting slurry was stirred over night at room temperature. The slurry was filtrated through celite and the filtrate was distilled off. To the remaining solution EtOAc was added. The organic layer was washed with water, saturated brine and concentrated, to give crude title compound, which was used directly in the next step. $^1$H NMR (DMSO-$d_6$): 10.13 (s, 1H), 8.08 (br s, 1H), 7.95 (m, 1H), 7.61 (m, 3H). MS ($M^+$+1)=208.

Example 5

1-[5-(3chlorophenyl)isoxazol-3-yl]ethanol

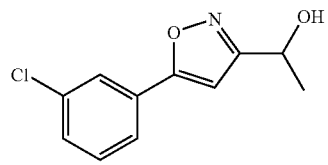

MeMgBr (3M in THF, 313 mL, 937.2 mmol) was added dropwise at 0° C. to 5-(3-chlorophenyl)isoxazole-3-carbaldehyde (177 g, 252 mmol) in THF (3 L). The mixture was allowed to attain room temperature, stirred at that temperature for 3 h and then quenched with aq. NH$_4$Cl at 0° C. and the solvent was distilled off. To the remaining was added EtOAc and filtered through a plug of celite. The organic layer was washed with water, saturated brine and concentrated. The crude product was purified by flash column chromatography on silica using heptane/EtOAc=80:20, to give the title compound (70 g, 37%) as a white-yellow solid. $^1$H NMR: 7.73 (m, 1H), 7.63 (m, 1H), 7.38 (m, 2H), 6.57 (s, 1H), 5.07 (q, 1H), 2.44 (s, 1H), 1.59 (d, 3H).

Example 6

(1R)-1-[5-(3-chlorophenyl)isoxazol-3-yl]ethyl acetate

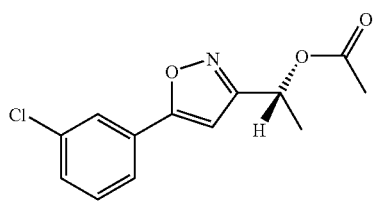

1-[5-(3-chlorophenyl)isoxazol-3-yl]ethanol (106.5 g, 476 mmol) and Novozyme 435® (13 g) are taken up under Ar in dry toluene (1.5 L). After addition of vinyl acetate (66 mL, 716 mmol) the reaction was run at r.t. over night, followed by filtration over celite and washing with DCM. The solvent was evaporated in vacuo and the crude product was subjected to column chromatography on silica using dichloromethane/methanol=20:1, to give the title compound (50 g, 47%). $^1$H NMR: 7.76 (m, 1H), 7.65 (m, 1H), 7.41 (m, 2H), 6.54 (s, 1H), 6.07 (q, 1H), 2.13 (s, 3H), 1.66 (d, 3H). LC-MS ($M^+$+1)=266.

Example 7

(1R)-1-[5-(3-chlorophenyl)isoxazol-3-yl]ethanol

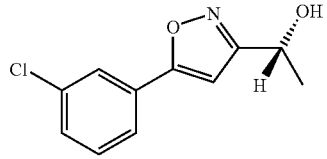

(1R)-1-[5-(3-chlorophenyl)isoxazol-3-yl]ethyl acetate (56 g, 211 mmol) and lithium hydroxide monohydrate (10.6 g, 253 mmol) were mixed with THF/Water (7/5, 1.2 L) and stirred at r.t. over night. Reducing the volume of the mixture in vacuo to about ½, followed by dilution with brine, extraction with ether and then drying over $MgSO_4$ and in vacuo concentration gave crude product. The crude product was purified by flash column chromatography on silica using heptane/EtOAc=70:30, to give the title compound (40 g, 85%). $^1$H NMR: 7.73 (m, 1H), 7.63 (m, 1H), 7.38 (m, 2H), 6.57 (s, 1H), 5.07 (q, 1H), 2.44 (s, 1H), 1.59 (d, 3H).

Example 8

2-Isonicotinoyl-N-methylhydrazinecarbothioamide

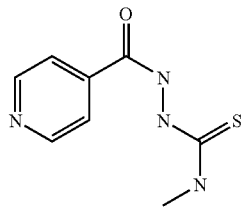

To a gently heated (35° C.) and mechanically stirred suspension of isonicotinohydrazide (435 g) in isopropyl alcohol (6.0 L) was added (methylimino)(thioxo)methane (230 g) in several small portions. After complete addition, the reaction mixture was heated (70° C.) for 6 h with an additional addition of isopropyl alcohol (600 ml) after 30 min. After cooling (ice-bath) the reaction mixture to 17° C., the obtained precipitate was filtered off and washed with isopropyl alcohol (1.0 L). This solid was then air-dried overnight to provide 615 g of the title compound as a white powder.

Example 9

4-Methyl-5-pyridin-4-yl-2,4-dihydro-3H-1,2,4-triazole-3-thione

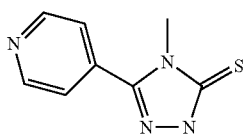

To a mechanically stirred suspension of 2-isonicotinoyl-N-methylhydrazinecarbothioamide (610 g) in water (5.0 L) was added sodium bicarbonate (390 g) at r.t. The reaction mixture was thereafter slowly heated to 70° C. over 2 h, and maintained at that temperature for another 3.5 h before cooling (ice-bath) to 17° C., followed by adjusting the pH to 3 by slow addition (over 90 min) of concentrated hydrochloric acid (ca. 470 mL). Subsequent filtration of the reaction mixture, followed by washing the collected solid with dilute hydrochloric acid (0.1 N, 2×1.0 L), gave a wet cake that was dried at 100 mbar under a gentle stream of air for 1.5 days to yield 544 g of the title compound.

Example 10

4-[4-Methyl-5-(methylthio)-4H-1,2,4-triazol-3-yl]pyridine

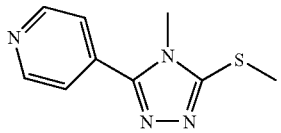

To a mechanically stirred and cooled (9° C.) suspension of 4-methyl-5-pyridin-4-yl-2,4-dihydro-3H-1,2,4-triazole-3-thione (267 g) and methyl iodide (197.7 g) in acetone (2.6 L), was added a solution of sodium hydroxide (54 g in 600 mL of water) at such a rate (ca. 20 mL/min) as to maintain the temperature between 10 and 15° C. Another portion of water (50 mL) was then added and the temperature was allowed to come to 21 to 24° C. After another 2 h, the acetone was distilled off from the reaction mixture in vacuo (water-bath kept at 30° C.). Another portion of water (750 mL) was then added before cooling (17 to 18° C.) and collection of the formed precipitate by filtration. This solid was then washed with water (2×1 L) before drying at 100 mbar under a gentle stream of air for 3 days to yield 235 g of the title compound as a white powder. $^1$H NMR (DMSO-$d_6$): 2.7 (s, 3H), 3.6 (s, 3H), 7.7 (m, 2H), 8.8 (d, 2H).

Example 11

4-[4-Methyl-5-(methylsulfonyl)-4H-1,2,4-triazol-3-yl]pyridine

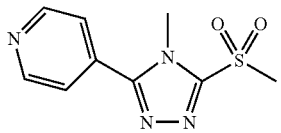

To a mechanically stirred solution of 4-[4-methyl-5-(methylthio)-4H-1,2,4-triazol-3-yl]pyridine (228 g) from the previous step, in a mixture of water (1.15 L) and acetic acid (1.15 L), was added portion-wise while cooling potassium permanganate (234 g), at such a rate as to maintain the temperature between 12 to 17° C. (ca. 45 min). The reaction mixture was then stirred at r.t. for 4 h before cooling on an ice-bath during the addition of a sodium hydroxide solution (5 N) over 2.5 h to set the pH to ca. 10. Dicalite® (100 g) and chloroform (1.6 L) was then added to the reaction mixture before filtration. The organic phase was separated from the filtrate and the aq. phase from the same was extracted with chloroform (2×1 L).

The filter-cake was extracted twice with chloroform (2×1.5 L). The combined organic phases were dried over magnesium sulfate, filtered, and concentrated in vacuo to provide 158 g of the title compound as a white powder. Another crop (78 g, white powder) was obtained by extraction of the filter cake with chloroform (2×2 L) and concentration of this solution in vacuo. $^1$H NMR (DMSO-$d_6$): 3.6 (s, 3H), 3.9 (s, 3H), 7.8 (s, 2H), 8.8 (s, 2H).

Example 12

3-[4-methyl-5-(methylsulfonyl)-4H-1,2,4-triazol-3-yl]pyridine

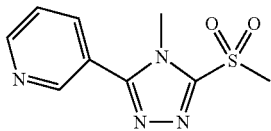

The title compound was prepared analogously to 4-[4-methyl-5-(methylsulfonyl)-4H-1,2,4-triazol-3-yl]pyridine as described herein, via the corresponding sequence consisting of the corresponding steps, by starting from nicotinohydrazide instead of isonicotinohydrazide. $^1$H NMR: 3.59 (s, 3H), 3.99 (s, 3H), 7.52 (m, 1H), 8.02 (dt, 1H), 8.83 (dd, 1H), 8.91 (m, 1H).

Synthesis of Final Compounds

Example 13

3-(5-{(1R)-1-[5-(3-chlorophenyl)isoxazol-3-yl]ethoxy}-4-methyl-4H-1,2,4-triazol-3-yl)pyridine

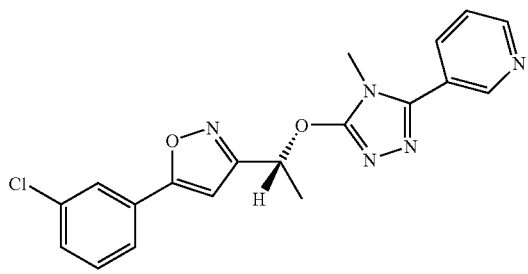

(1R)-1-[5-(3-chlorophenyl)isoxazol-3-yl]ethanol (5.40 g, 24.1 mmol) was dissolved in DMF (45 mL). To this 3-[4-methyl-5-(methylsulfonyl)-4H-1,2,4-triazol-3-yl]pyridine (5.75 g, 24.1 mmol) and cesium carbonate (10.1 g, 31.4 mmol) were added. After stirring over night at 60° C., water was added. The mixture was extracted with dichloromethane, followed by concentration of the organic layer in vacuo, to give a crude which was purified by column chromatography on silica using dichloromethane/methanol=98/2, to give the title compound (7.10 g, 77%). $^1$H NMR: 8.90 (d, 1H), 8.72 (m, 1H), 8.04 (dt, 1H), 7.76 (bs, 1H), 7.66 (m, 1H), 7.45 (m, 1H), 7.40 (m, 2H), 6.73 (s, 1H), 6.35 (q, 1H), 3.57 (s, 3H), 1.93 (d, 3H). $^1$H NMR (DMSO-$d_6$): 8.90 (d, 1H), 8.71 (dd, 1H), 8.13 (dt, 1H), 7.99 (s, 1H), 7.86 (m, 1H), 7.58 (m, 3H), 7.40 (s, 1H), 6.19 (q, 1H), 3.54 (s, 3H), 1.81 (d, 3H). LC-MS (M$^+$+1)=382. $[\alpha]_D^{RT}$ (2.92 g/L, CDCl$_3$)=−46.575°

Example 14

4-(5-{(rac)-1-[5-(3-chlorophenyl)isoxazol-3-yl]ethoxy}-4-methyl-4H-1,2,4-triazol-3-yl)pyridine

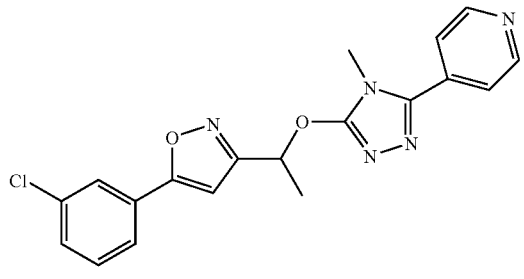

1-[5-(3-chlorophenyl)isoxazol-3-yl]ethanol (63.4 mg, 0.28 mmol), DMF and sodium hydride (60% dispersion in oil, 15.1 mg, 0.38 mmol) were mixed under inert atmosphere and stirred at r.t for 1 h, followed by addition of 4-[4-methyl-5-(methylsulfonyl)-4H-1,2,4-triazol-3-yl]pyridine (45 mg, 0.19 mmol). After stirring at 80° C. for 24 h, the mixture was cooled to r.t., diluted with EtOAc and washed with water and brine. The organic phase was dried (Na$_2$SO$_4$), filtered and concentrated in vacuo. The crude residue was purified via column chromatography on silica using 5% methanol in EtOAc to isolate the title compound (11.7 mg). $^1$H-NMR: 8.81 (bs, 2H), 7.77 (s, 1H), 7.67 (m, 3H), 7.42 (m, 2H), 6.73 (s, 1H), 6.36 (q, 1H), 3.62 (s, 3H), 1.94 (d, 3H).

Example 15

4-(5-{(1R)-1-[5-(3-chlorophenyl)isoxazol-3-yl]ethoxy}-4-methyl-4H-1,2,4-triazol-3-yl)pyridine

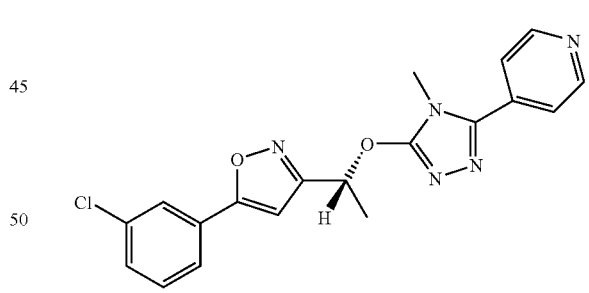

Method 1:
Preparative chiral HPLC separation of 4-(5-{(rac)-1-[5-(3-chlorophenyl)isoxazol-3-yl]ethoxy}-4-methyl-4H-1,2,4-triazol-3-yl)pyridine on chiralpak AD column with isopropanol as eluent, yielded the title compound as the first eluting enantiomer.

Method 2:
The title compound was prepared analogous to 3-(5-{(1R)-1-[5-(3-chlorophenyl)isoxazol-3-yl]ethoxy}-4-methyl-4H-1,2,4-triazol-3-yl)pyridine, by coupling of (1R)-1-[5-(3-chlorophenyl)isoxazol-3-yl]ethanol with 4-[4-methyl-5-(methylsulfonyl)-4H-1,2,4-triazol-3-yl]pyridine employing cesium carbonate in DMF. $^1$H NMR (DMSO-d$_6$): 8.73 (m, 2H), 7.97 (br. s, 1H), 7.85 (m, 1H), 7.74 (m, 2H), 7.58 (m, 2H), 7.39 (s, 1H), 6.20 (q, 1H), 3.60 (s, 3H), 1.81 (d, 3H). $[\alpha]_D^{RT}$ (5.827 g/L, CDCl$_3$)=−48.567°

Example 16

4-(5-{(1S)-1-[5-(3-chlorophenyl)isoxazol-3-yl]ethoxy}-4-methyl-4H-1,2,4-triazol-3-yl)pyridine

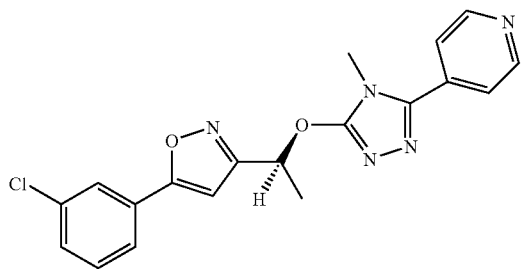

The title compound was isolated as the second eluting enantiomer in preparative chiral HPLC separation as described in the example of 4-(5-{(1R)-1-[5-(3-chlorophenyl)isoxazol-3-yl]ethoxy}-4-methyl-4H-1,2,4-triazol-3-yl)pyridine (method 1). $^1$H-NMR: 8.81 (bs, 2H), 7.77 (s, 1H), 7.67 (m, 3H), 7.42 (m, 2H), 6.73 (s, 1H), 6.36 (q, 1H), 3.62 (s, 3H), 1.94 (d, 3H).

Example 17

4-(5-{(1R)-1-[5-(3chlorophenyl)isoxazol-3-yl]ethoxy}-4-methyl-4H-1,2,4-triazol-3-yl)pyridine hydrochloride The title salt was manufactured by adding 10 μl of a 32 wt-% aqueous HCl solution in two portions to a clear solution of 35 mg 4-(5-{(1R)-1-[5-(3-chlorophenyl)isoxazol-3-yl]ethoxy}-4-methyl-4H-1,2,4-triazol-3-yl)pyridine free base in 500 μl ethanol at 50° C. The slurry was cooled to 10° C. and kept over night under agitation before the salt was filtered off, washed with 500 μl ethanol and dried at room temperature under vacuum.

The salt was crystalline, had a clear melting behavior and had an increased moisture sorption at 90-95% RH.

The title salt was manufactured again in a similar way in ethanol, 2-propanol and ethyl acetate and also at 1 g scale in ethanol. All batches produced the same crystal modification, although the amorphous content was slightly higher in some batches. The melting point was from 150° C. to 160° C.

The salt manufactured at 1 g scale from ethanol was further investigated for its intrinsic dissolution rate and compared to the free base of 4-(5-{(1R)-1-[5-(3-chlorophenyl)isoxazol-3-yl]ethoxy}-4-methyl-4H-1,2,4-triazol-3-yl)pyridine. The salt had a 1000 times higher intrinsic dissolution rate as compared to the free base. Dissolution rates of the base and salt were measured with a low-volume rotating disc method. Discs were compressed from pure compound and centrically mounted in a disc holder with an exposed area of 0.07 cm$^2$. The disc holder rotated at 500 rpm immersed in 50 mL USP Phosphate buffer pH 6.8 at 37° C. The compound was analyzed UV-Online by a Spectrophotometer with a flow cell and a peristaltic pump with continuous circulation.

Example 18

4-(5-{(1R)-1-[5-(3-chlorophenyl)isoxazol-3-yl]ethoxy}-4-methyl-4H-1,2,4-triazol-3-yl)pyridine sulphate An oiled salt was manufactured by evaporating a clear solution obtained by mixing 500 μl water with 33 mg 4-(5-{(1R)-1-[5-(3-chlorophenyl)isoxazol-3-yl]ethoxy}-4-methyl-4H-1,2,4-triazol-3-yl)pyridine free base, 500 μl methanol and 7 μl 98 wt-% sulphuric acid. The title salt was manufactured by recrystallising the oiled salt in 500 μl ethanol.

The title salt was crystalline with essential amorphous content, had no clear melting behavior and deliquesce at 60-70% relative humidity.

The title salt was manufactured again by adding three portions of 5 μl concentrated sulphuric acid (98%) over 1.5 h to a clear solution of 66-68 mg 4-(5-{(1R)-1-[5-(3-chlorophenyl)isoxazol-3-yl]ethoxy}-4-methyl-4H-1,2,4-triazol-3-yl)pyridine free base in 1 ml 2-propanol or 1 ml ethanol at 68° C. The salt manufactured from ethanol had a melting point of 128° C. although it deliquesce at 70-80% RH.

Biological Evaluation

Functional Assessment of mGluR5 Antagonism in Cell Lines Expressing mGluR5D

The properties of the compounds of the invention can be analyzed using standard assays for pharmacological activity. Examples of glutamate receptor assays are well known in the art as described in for example Aramori et al., Neuron 8:757 (1992), Tanabe et al., Neuron 8:169 (1992), Miller et al., J. Neuroscience 15:6103 (1995), Balazs, et al., J. Neurochemistry 69:151 (1997). The methodology described in these publications is incorporated herein by reference. Conveniently, the compounds of the invention can be studied by means of an assay (FLIPR) that measures the mobilization of intracellular calcium, [Ca$^2$]$_i$ in cells expressing mGluR5 or another assay (IP3) that measures inositol phosphate turnover.

FLIPR Assay

Cells expressing human mGluR5d as described in WO97/05252 are seeded at a density of 100,000 cells per well on collagen coated clear bottom 96-well plates with black sides and experiments are done 24 h following seeding. All assays are done in a buffer containing 127 mM NaCl, 5 mM KCl, 2 mM MgCl$_2$, 0.7 mM NaH$_2$PO$_4$, 2 mM CaCl$_2$, 0.422 mg/ml NaHCO$_3$, 2.4 mg/ml HEPES, 1.8 mg/ml glucose and 1 mg/ml BSA Fraction IV (pH 7.4). Cell cultures in the 96-well plates are loaded for 60 minutes in the above mentioned buffer containing 4 μM of the acetoxymethyl ester form of the fluorescent calcium indicator fluo-3 (Molecular Probes, Eugene, Oreg.) in 0.01% pluronic acid (a proprietary, non-ionic surfactant polyol—CAS Number 9003-11-6). Following the loading period the fluo-3 buffer is removed and replaced with fresh assay buffer. FLIPR experiments are done using a laser setting of 0.800 W and a 0.4 second CCD camera shutter speed with excitation and emission wavelengths of 488 nm and 562 nm, respectively. Each experiment is initiated with 160 μl of buffer present in each well of the cell plate. A 40 μl addition from the antagonist plate was followed by a 50 μL addition from the agonist plate. A 90 second interval separates the antagonist and agonist additions. The fluorescence signal is sampled 50 times at 1 second intervals followed by 3 samples at 5 second intervals immediately after each of the two additions. Responses are measured as the difference between the peak height of the response to agonist, less the background fluorescence within the sample period. $IC_{50}$ determinations are made using a linear least squares fitting program.

IP3 Assay

An additional functional assay for mGluR5d is described in WO97/05252 and is based on phosphatidylinositol turnover. Receptor activation stimulates phospholipase C activity and leads to increased formation of inositol 1,4,5,triphosphate ($IP_3$).

GHEK stably expressing the human mGluR5d are seeded onto 24 well poly-L-lysine coated plates at $40 \times 10^4$ cells/well in media containing 1 μCi/well [3H] myo-inositol. Cells were incubated overnight (16 h), then washed three times and incubated for 1 h at 37° C. in HEPES buffered saline (146 mM NaCl, 4.2 mM KCl, 0.5 mM $MgCl_2$, 0.1% glucose, 20 mM HEPES, pH 7.4) supplemented with 1 unit/ml glutamate pyruvate transaminase and 2 mM pyruvate. Cells are washed once in HEPES buffered saline and pre-incubated for 10 min in HEPES buffered saline containing 10 mM LiCl. Compounds are incubated in duplicate at 37° C. for 15 min, then either glutamate (80 μM) or DHPG (30 μM) is added and incubated for an additional 30 min. The reaction is terminated by the addition of 0.5 ml perchloric acid (5%) on ice, with incubation at 4° C. for at least 30 min. Samples are collected in 15 ml polyproplylene tubes and inositol phosphates are separated using ion-exchange resin (Dowex AG1-X8 formate form, 200-400 mesh, BIORAD) columns. Inositol phosphate separation was done by first eluting glycero phosphatidyl inositol with 8 ml 30 mM ammonium formate. Next, total inositol phosphates is eluted with 8 ml 700 mM ammonium formate/100 mM formic acid and collected in scintillation vials. This eluate is then mixed with 8 ml of scintillant and [3H] inositol incorporation is determined by scintillation counting. The dpm counts from the duplicate samples are plotted and $IC_{50}$ determinations are generated using a linear least squares fitting program.

ABBREVIATIONS

BSA Bovine Serum Albumin
CCD Charge Coupled Device
CRC Concentration Response Curve
DHPG 3,5-dihydroxyphenylglycine
DPM Disintegrations per Minute
EDTA Ethylene Diamine Tetraacetic Acid
FLIPR Fluorometric Imaging Plate reader
GHEK GLAST-containing Human Embrionic Kidney
GLAST glutamate/aspartate transporter
HEPES 4-(2-hydroxyethyl)-1-piperazineethanesulfonic acid (buffer)
$IP_3$ inositol triphosphate Generally, the compounds were active in the assay above with $IC_{50}$ values less than 10 000 nM. In one aspect of the invention, the $IC_{50}$ value is less than 1 μM. In a further aspect of the invention, the $IC_{50}$ value is less than 100 nM.

Screening for Compounds Active Against TLESR

Adult Labrador retrievers of both genders, trained to stand in a Pavlov sling, are used. Mucosa-to-skin esophagostomies are formed and the dogs are allowed to recover completely before any experiments are done.

Motility Measurement

In brief, after fasting for approximately 17 h with free supply of water, a multilumen sleeve/sidehole assembly (Dentsleeve, Adelaide, South Australia) is introduced through the esophagostomy to measure gastric, lower esophageal sphincter (LES) and esophageal pressures. The assembly is perfused with water using a low-compliance manometric perfusion pump (Dentsleeve, Adelaide, South Australia). An air-perfused tube is passed in the oral direction to measure swallows, and an antimony electrode monitored pH, 3 cm above the LES. All signals are amplified and acquired on a personal computer at 10 Hz.

When a baseline measurement free from fasting gastric/LES phase III motor activity has been obtained, placebo (0.9% NaCl) or test compound is administered intravenously (i.v., 0.5 ml/kg) in a foreleg vein. Ten min after i.v. administration, a nutrient meal (10% peptone, 5% D-glucose, 5% Intralipid, pH 3.0) is infused into the stomach through the central lumen of the assembly at 100 ml/min to a final volume of 30 ml/kg. The infusion of the nutrient meal is followed by air infusion at a rate of 500 ml/min until an intragastric pressure of 10±1 mmHg is obtained. The pressure is then maintained at this level throughout the experiment using the infusion pump for further air infusion or for venting air from the stomach. The experimental time from start of nutrient infusion to end of air insufflation is 45 min. The procedure has been validated as a reliable means of triggering TLESRs.

TLESRs is defined as a decrease in lower esophageal sphincter pressure (with reference to intragastric pressure) at a rate of >1 mmHg/s. The relaxation should not be preceded by a pharyngeal signal ≦2 s before its onset in which case the relaxation is classified as swallow-induced. The pressure difference between the LES and the stomach should be less than 2 mmHg, and the duration of the complete relaxation longer than 1 s.

The invention claimed is:

1. A compound of formula II

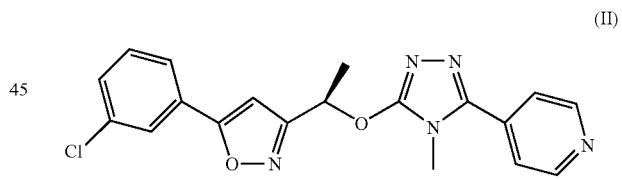

(II)

as well as a pharmaceutically acceptable salt thereof.

2. A compound according to claim 1 in crystalline form.

3. The compound 4-(5-{(1R)-1-[5-(3-chlorophenyl)isoxazol-3-yl]ethoxy}-4-methyl-4H-1,2,4-triazol-3-yl)pyridine hydrochloride.

4. The compound 4-(5- {(1R)-1-[5-(3-chlorophenyl)isoxazol-3-yl]ethoxy}-4-methyl-4H- 1,2,4-triazol-3-yl)pyridine sulphate.

5. A pharmaceutical composition comprising a compound according to any one of claims 1, 2, 3 or 4 as an active ingredient, together with a pharmacologically and pharmaceutically acceptable carrier.

* * * * *